(12) United States Patent
Rosende

(10) Patent No.: US 11,385,477 B2
(45) Date of Patent: Jul. 12, 2022

(54) METHOD FOR DESIGNING A PAIR OF OPTHALMIC LENSES AND DEVICE FOR OPTICAL MEASUREMENTS

(71) Applicant: Lentitech, S.L., Vizcaya (ES)

(72) Inventor: Julio Villaverde Rosende, Villarcayo (ES)

(73) Assignee: LENTITECH, S.L., Vizcaya (ES)

( * ) Notice: Subject to any disclaimer, the term of this patent is extended or adjusted under 35 U.S.C. 154(b) by 155 days.

(21) Appl. No.: 16/497,841

(22) PCT Filed: Mar. 29, 2018

(86) PCT No.: PCT/ES2018/070282
§ 371 (c)(1),
(2) Date: Sep. 26, 2019

(87) PCT Pub. No.: WO2018/178493
PCT Pub. Date: Oct. 4, 2018

(65) Prior Publication Data
US 2020/0103674 A1 Apr. 2, 2020

(30) Foreign Application Priority Data
Mar. 30, 2017 (ES) ................ ES201730494

(51) Int. Cl.
*G02C 7/02* (2006.01)
*G02C 7/16* (2006.01)
(Continued)

(52) U.S. Cl.
CPC ............... *G02C 7/027* (2013.01); *A61B 3/02* (2013.01); *A61B 3/08* (2013.01); *A61B 3/18* (2013.01); *G02C 7/165* (2013.01); *G02C 13/005* (2013.01)

(58) Field of Classification Search
CPC .... A61B 3/02; A61B 3/08; A61B 3/18; A61B 3/156; A61B 3/0075; A61B 3/0091;
(Continued)

(56) References Cited

U.S. PATENT DOCUMENTS 4,190,331 A 2/1980 Padula, I
4,252,419 A * 2/1981 Padula, II ................ A61B 3/11
33/200
(Continued)

FOREIGN PATENT DOCUMENTS

| DE | 1833415 | 6/1961 |
|---|---|---|
| DE | 3043668 | 6/1982 |
| DE | 19929958 | 11/2000 |

OTHER PUBLICATIONS

International Search Report, PCT/ES2018/070282, dated Oct. 1, 2018.

*Primary Examiner* — Jordan M Schwartz
(74) *Attorney, Agent, or Firm* — Lucas & Mercanti, LLP

(57) ABSTRACT

Method for designing a pair of ophthalmic lenses and device for optical measurements. The method comprises: determining a distance and placing an object (100) at said distance; placing a frame (4) of reference on the user; for each eye: keeping it uncovered and covering the other eye; placing in front of the eye a screen (5, 6) with a through hole (520, 620); shifting the position of the hole (520, 620) until the user sees said object (100) looking through the hole (520, 620), so that said object (100) is centred in the field of view available; uncovering both eyes; adjusting the positions of the holes (520, 620), to obtain binocular vision; and designing each lens (510, 610) according to said position. The device (1) comprises a frame (2) to which, for each eye, a first plate (51, 61) having a vertical groove (53, 63) and a second plate (52, 62) having a horizontal groove (54, 64) are
(Continued)

attached and can be shifted. So that, when the grooves overlap, a pinhole (55, 65) is formed.

18 Claims, 5 Drawing Sheets

(51) Int. Cl.
*A61B 3/02* (2006.01)
*A61B 3/08* (2006.01)
*A61B 3/18* (2006.01)
*G02C 13/00* (2006.01)

(58) Field of Classification Search
CPC ......... A61B 3/028; A61B 3/132; A61B 3/135; G02C 7/027; G02C 7/165; G02C 13/005
USPC .................. 351/201, 233, 240, 222, 244
See application file for complete search history.

(56) References Cited

U.S. PATENT DOCUMENTS

| | | | | |
|---|---|---|---|---|
| 4,368,958 A | * | 1/1983 | Buget | G02C 13/005 |
| | | | | 33/200 |
| 4,407,571 A | * | 10/1983 | Augusto | A61B 3/0083 |
| | | | | 351/211 |
| 4,838,676 A | * | 6/1989 | Buget | A61B 3/08 |
| | | | | 351/202 |
| 5,461,434 A | * | 10/1995 | Blattberg | A61B 3/111 |
| | | | | 351/204 |
| 6,132,045 A | * | 10/2000 | Gauvreau | A61B 3/111 |
| | | | | 351/200 |
| 2007/0285620 A1 | | 12/2007 | Clark | |
| 2018/0020911 A1 | * | 1/2018 | White | A61B 3/028 |
| | | | | 351/227 |

\* cited by examiner

METHOD FOR DESIGNING A PAIR OF OPTHALMIC LENSES AND DEVICE FOR OPTICAL MEASUREMENTS

FIELD OF THE INVENTION

The invention lies in the field of ophthalmic lenses.

More specifically, the invention relates to a method for designing a pair of ophthalmic lenses, each lens corresponding to one eye of a user.

The invention also relates to a device for optical measurements, comprising a frame having a wearing position, wherein a user wears said device in front of the eyes, defining an inner side facing said eyes, and an outer side opposite to said inner side, said device having first frame supporting means.

STATE OF THE ART

In the field of corrective lenses, the so-called monofocal lenses are intended to correct visual defects of a user, generally for a specific viewing distance. There are bifocal glasses with two areas of vision (for example, one for far vision and the other for near vision) and two optical centres, or even multifocal lenses for multiple viewing distances. A particular case are the so-called progressive lenses which generally are designed for far vision and near vision, and wherein there is an intermediate area between the optical centre for far vision and the optical centre for near vision, which gradually changes, and allows adapting to different intermediate distances. In this case, the horizontal distance between the far and near optical centre is known as inset, while the vertical distance is known as corridor length.

In association with lenses, the focal distance or focal length of a lens is the distance between the optical centre of the lens and the focus, also called focal point. The focal distance can have positive or negative values. Said focal point is the point where the parallel rays crossing the lens converge, in the case of converging lenses. Or an imaginary point from which the beams of light that pass through the lens seem to emerge, in the case of diverging lenses. In the first case, the focal distance is positive, while in the second case the focal distance is negative. The power of a lens is the inverse of the focal distance, and it is measured in dioptres ($m^{-1}$).

Thus, the prescription of the power of the lens that permits correct vision for the viewing distance for which the lenses are designed, is usually made by a professional, using usual devices and methods in the art to reach correct dioptre values in each case and for each eye, obtaining a pair of lenses that are assembled in spectacles.

Effectively, said professional takes some measurements of a user so that he/she can prescribe suitable lenses therefor. In the design stage, among other aspects, the type of corrective lens is determined (for example, for myopia, hyperopia, presbyopia, etc.), its power (measured in dioptres), and the optical centre of said lens. Note that this optical centre of the lens can also shift to achieve an effect equivalent to a prism whose power in dioptres is proportional to said shift distance and the power of the lens. This is known as Prentice's Law.

In the known art, the optical centre is determined using two main ways: through pre-established standard positions or through specific measurements. The first case, although it has advantages such as the mass production of lenses, is not too adaptable for some users, especially in the case where there is facial asymmetry or another kind of conditioning factors that shift the location of the optical centre with respect to said standard position. In the second case, the usual methods start with observing the location of the user's pupils when looking at an object located at a viewing distance for which the lenses are designed. In this case, by projecting the imaginary line that joins the object to the centres of each retina, this line crosses the geometrical axis of the eye and it is possible to determine the point where it would cross the lens, when the lens in its wearing position in a spectacles frame.

A skilled in the art will understand that in the cases of bifocal, multifocal or progressive lenses, the measurement is repeated for the viewing distances required by the lens.

For the sake of clarity and brevity, in the context of this invention one viewing distance will be discussed, however, a person skilled in the art will be able to apply the same considerations in the case of bifocal, multifocal or progressive lenses.

This way, the existing methods for designing ophthalmic lenses in the state of the art that are based on measurements are aimed at determining the optimum position of the optical centre of each lens for a viewing distance. As mentioned above, this is done mainly based on the positions of the user's pupils when he/she looks at a reference object located at a viewing distance. However, in order to obtain the position of the optical centres through trigonometry rules, it is also necessary to know the specific shape of the eye and its different parts, and values such as the location of the fovea are particularly necessary.

Fovea is known as the area of the retina where the light rays are focused and it is particularly capable of colour vision. Thus, directing sight towards an object means placing its optical image on the fovea. However, the position of the fovea within the eye is not aligned with its geometrical axis. Indeed, in the art the Kappa angle is known as the angle between:

a geometrical axis of the eye, which passes through the geometrical centre of the pupil of said eye; and an optical axis of the eye, which joins the central fovea of the retina of said eye to said point located at the viewing distance. This optical axis also receives the name of foveal fixation axis.

Therefore, in the known art, instead of using the imaginary line mentioned above which is based on the geometrical eye, it is corrected using said Kappa angle.

Unfortunately, some of these data are very difficult and even impossible to measure in vivo during an external exploration of the user. In some cases, these measurements would require surgical interventions or exploratory equipment that is not usually available in the field of optometry, such as X-ray apparatus, ultrasounds, etc. Consequently, in the art, it is usual to use standard values for this data, for example, for emmetrope users a Kappa angle of about 5° is considered, for hypermetropic users up to 10° or more, and for myopic users the Kappa angle reaches 2°.

This impossibility of real and personalised measurements for each user results in determining optical centres for lenses which may not completely coincide with the user's real vision axes. This means that the lens is shifted with respect to the position that the user would really need. In the cases where the shift is not very large, the user can manage to accommodate the vision, although side effects such as headaches or visual fatigue may appear. In more serious cases, users can end up losing their binocular vision, have blurred vision, etc.

For this reason, a method for designing ophthalmic lens is necessary, which allows obtaining greater accuracy in locating the optical centres of the lenses, and which is adaptable to each user for whom said lenses are designed.

Description of the Invention

Below, there is a description of some common concepts relative to the invention disclosed in this document. Unless otherwise indicated, it will be understood that the directions are relative to the user when he/she is standing. In this respect, the horizontal direction is the one that goes from the right side to the left side of the user or vice versa. The vertical direction is the one that is parallel to the user's vertical.

The references to far vision or near vision, must be understood as referring to the situations where a user looks at a point located at a far distance or a near distance, respectively. On the other hand, when referring to binocularity, binocularity conditions or binocular vision, it must be understood that the user's brain is capable of merging the images from both eyes, so that it reaches a perception of the depth. On the contrary, reference is made to diplopia, dissociated vision, dissociation conditions or a dissociated form of vision, when the images formed in each eye do not fuse, and so a perspective image is not obtained.

When in binocular vision, the fovea of an eye corresponds to a small area centred in the fovea of the other eye, called Panum's area. Thus, to each point of the retina of an eye, there corresponds a small area of the other eye. This way, if one eye deviates, the patient will not show diplopia as long as the image falls inside the Panum's Area.

Fixation disparity is the name given to the different alignment in the visual axes, which permits sensory merging. When the magnitude of the fixation disparity is small, the object is projected within Panum's areas of fusion, while if the fixation disparity is large, it could mean abnormal causes or visual problems.

The deviation can occur both in one eye and in two, and it can be physiological or the result of stress on the binocular vision. Associated phoria is known as the power of the prism needed to neutralise said fixation disparity. In this respect, the fixation disparity and associated phoria measurements are equivalent as one implies the other.

For their part, the ophthalmic lenses are intended to be mounted in spectacles, supported by a frame. Thus, the wearing position is determined by said frame, the shape of the lenses and the angles at which they are related to the user, with the main ones being the pantoscopic angle (with respect to the vertical) and the frame wrap angle (with respect to the horizontal). In the art, the usual way to determine the position of an optical centre comprises two distances: a horizontal distance referenced to the bisecting nasal plane, this being the vertical plane that divides the bridge of the user's nose; and a vertical distance. Said vertical distance corresponds to the height with respect to the lower end of the lens, with said lower end being located on a vertical line centred along said horizontal distance. The person skilled in the art will understand that these measurements must be considered in the wearing position of the lenses in the frame.

The object of the invention is to provide a method for designing a pair of ophthalmic lenses of the type indicated at the beginning, which allows overcoming the problems mentioned above.

This purpose is achieved by means of a method for designing a pair of ophthalmic lenses of the type indicated at the beginning, characterized in that it comprises a measurement stage comprising the following steps:

[a] determining a viewing distance and placing a reference object at a point located at said viewing distance;
[b] putting a reference spectacles frame on a user, configured to determine a wearing position of said lenses;
[c] for a first eye of the user:
 [1] keeping said eye uncovered and cover the other eye;
 [2] placing in front of said eye a screen corresponding to said eye, having a through hole corresponding to said eye;
 [3] shifting the position of said hole until the user sees said object looking through said hole, so that said object is centred in the field of view that said hole allows;
[d] repeating steps [c.1] to [c.3] for the second eye;
[e] uncovering both eyes;
[f] in the event that the user sees, in a dissociated way, two areas corresponding to said holes corresponding to said first eye and to said second eye adjusting the position of said holes, so that both images fuse, thus obtaining binocular vision;
[g] for each hole corresponding to an eye and to a lens, taking a measurement of the position of said hole with respect to said wearing position of said lens; and
[h] Designing each lens corresponding to one eye for said viewing distance according to said position of said hole corresponding to said eye.

This way, the measurement comes from a subjective observation by the user, whereby the line that joins each through hole to the reference object coincides with the foveal fixation axis. Therefore, it is not necessary to make any assumption regarding the position of the fovea in the eye. Effectively, the point at which said foveal attachment axis crosses said wearing position where the lens will be, indicates the location of the optical centre of the lens for said viewing distance. This results in a lens design with a much more accurate and personalized configuration for said user. The skilled person in the art will understand that the method can be repeated for different viewing distances, for example, in the case of bifocal, multifocal or progressive lenses. Also, steps [c] to [f] can be repeated to obtain a progressive adjustment for the same viewing distance, so that the position of the holes is adjusted iteratively.

In the context of the invention, and unless otherwise indicated, the step of placing a reference object at a point located at said viewing distance preferably comprises placing it at said distance and in a preferential wearing position for the user for said viewing distance. For example, for a far viewing distance the user usually looks directly forward at the height of the eyes. However, the near viewing distance is associated with tasks such as reading a book. In this case, the object is preferably placed in relation to the user in the place where said book would be located. Although this effect is more common in near vision, there are also users who with far vision tend to tilt their head and/or rotate their eyes. This methodology has the advantage of greater personalisation of the lenses for the user, since the design takes into consideration the use and the preferential postures of the user who will use said lenses.

The person skilled in the art will understand that the fact of covering one eye can be done in different ways, although preferably it comprises the actual user closing said eye, covering it with his/her eyelid. Also, said screen preferably comprises one or more overlapped plates so that the through hole of each screen communicates both sides of the plates. Besides, the screen is preferably not transparent, so that it is easier for the user to determine which part of the view is contained in said hole. In other preferred embodiments, the screen is transparent, which allows the professional who takes the measurements to observe the user's eye, which is useful for conducting an ophthalmic diagnosis, and also for helping the user to find the reference object. On the other hand, said hole is preferably a pinhole hole, although slots are not excluded.

With respect to the reference object, this preferably comprises a central element, horizontal guides and vertical guides. Preferably, said guides are a horizontal ruler and a vertical ruler, or a reticular guide. This way, it is easier for the user to centre the visual point through the hole, which improves the accuracy of the design.

On the basis of the invention defined in the main claim, some preferred embodiments have been envisaged which characteristics are included in the dependent claims.

Preferably, each one of said holes is a pinhole hole with a diameter preferably between 0.2 mm and 5 mm, more preferably between 0.4 mm and 0.6 mm, even more preferably 0.5 mm. Said hole can have different geometrical shapes, not only circular. In this respect, the diameter is considered in a broad sense, corresponding to the straight longest segment between the ones that join two points of the perimeter of the hole across the centre of said hole. Very large diameters suffer from the disadvantage of lost accuracy, while smaller diameters hinder vision and end up producing unwanted diffractions. It has been proven in experiments that these values provide favourable viewing conditions without losing accuracy excessively.

Preferably, for each eye, said screen for said eye comprises a first plate, having a vertical through groove, and a second plate, overlapping said first plate and having a horizontal through groove, so that said pinhole hole is formed by the overlap between said vertical groove and said horizontal groove, and wherein steps [c] to [f] break down into a stage for determining the horizontal position, comprising the following steps:

[c'] for a first eye of the user:
  [1] keeping said eye uncovered and covering the other eye;
  [2] placing said first plate in front of said eye;
  [3] shifting said first plate until the user sees the object looking through said vertical groove, so that said object is centred in the field of view that said vertical groove allows;
[d'] repeating steps [c'.1] to [c'.3] for a second eye;
[e'] uncovering both eyes; and
[f'] in the event that the user sees, in a dissociated way, two vertical strips corresponding to said vertical grooves, adjusting the position of said first plates, so that both images fuse, thus obtaining binocular vision;

and a stage for determining the vertical position, comprising the following steps:

[c"] for a first eye of a user:
  [1] keeping said eye uncovered and covering the other eye;
  [2] placing said second plate in front of said eye, overlapping said first plate;
  [3] shifting said second plate until the user sees said object by looking through said pinhole, so that said object is centred in the field of view that said pinhole allows;
[d"] repeating steps [c".1] to [c".3] for the second eye;
[e"] uncovering both eyes; and
[f"] in the event that the user sees, in a dissociated way, two visual points corresponding to said pinholes, adjusting the position of said second plates, so that both images fuse, thus obtaining binocular vision.

Therefore, the vision is adjusted in two stages, one for the horizontal position and another for the vertical position. This has the advantage that it is easier to locate the reference object, even if the grooves are narrow. This obtains greater accuracy together with easier usage. Preferably, in the stage corresponding to the horizontal position, each vertical groove is placed in the point furthest away from the bisecting nasal plane and it is made to converge until the reference object is located. The person skilled in the art will understand that the order of the stages described above is only a preferred way, and that the same results can be obtained by starting with the stage for the vertical position followed by the stage for the horizontal position. In this latter case, the pinhole would be formed in the horizontal stage. The person skilled in the art will also understand that, although here we are talking about vertical and horizontal grooves, this does not exclude the fact that said grooves are tilted. Indeed, the necessary condition is that in the first stage the groove facilitates the location of the reference object by the user and that in the second stage, the next groove forms a pinhole by overlapping the groove used in the first stage. Preferably, both plates have a reduced thickness, between 0.2 mm and 2 mm, preferably 0.5 mm, so that the passage channel of the pinhole also has a reduced length, thus minimizing the effects of diffraction, and allowing a greater range of angles for the possible vision axes crossing said hole. For similar reasons, the plates are preferably in contact with one another.

Preferably, in the event that in the points [f], [f'] or [f"] the user is not able to make both images to fuse, the method further comprises the following additional steps:

taking a measurement of the associated phoria for said viewing distance;
determining a prism necessary for said associated phoria;
repeating the measurement with the presence of said prism; and
designing said pair of lenses for said viewing distance also according to said prism.

If the user does not manage to make both images converge in a way that produces binocular vision, this may indicate the presence of a fixation disparity. This condition can be resolved generally by using prisms. In particular, the prism that compensates the fixation disparity is called associated phoria. This way, once the problem of the user's fixation disparity has been resolved for said distance by means of said prism, the method can be repeated, so that the conditions of binocularity can be achieved in points [f], [f'] or [f"]. The lenses designed this way, will also contain the prism necessary to compensate the fixation disparity. The person skilled in the art will understand that, although for the sake of simplicity we talk about a prism, the fixation disparity can actually occur both in the horizontal and in the vertical direction, and so said prism can have various components.

Preferably, said measurement of the associated phoria is taken in one of the points [e], [e'] or [e"], or [f], [f'] or [f"], comprising the following additional steps:

placing in front of one of the eyes a prism having a known prismatic power, said prism being overlapped with said hole;
repeating the above point with prisms having different prismatic powers until making the images from both eyes fuse; and
determining said prism necessary for said associated phoria as the prism that makes the images from both eyes fuse.

Therefore, the elements used in the method of the invention can be used to measure the associated phoria, or what is the equivalent, the prism needed to compensate the fixation disparity. This simplifies the process and increases the user's comfort. Preferably, the prism is placed on the side of said hole furthest away from said eye, i.e., on the outside, which has the advantage of not moving the position of the holes away from the wearing position of the lenses.

Preferably, a colour filter is previously placed in the line of sight of one of said eyes, thereby making it easier to obtain dissociated vision. In particular, it is convenient to force dissociated vision when the phoria is determined, as this allows determining exactly the prism that allows binocularity. A person skilled in the art will understand that in the case of dissociated vision we are not talking about associated phoria, as the latter is necessary in conditions of associated vision. So, for some users it is necessary to compensate said phoria, for example, by using prisms, in order to be able to guarantee the binocularity conditions. Preferably, said colour filter is a red filter, which it has been noted to allow dissociating the image.

The invention also relates to a device for optical measurements aimed at facilitating the measurements necessary for said design method.

This purpose is achieved by means of a device for optical measurements of the type indicated at the beginning, characterized in that it also comprises:
 a right screen, corresponding to the right eye of a user, comprising a first right plate and a second right plate, and
 a left screen, corresponding to the left eye of a user, comprising a first left plate and a second left plate,
wherein for each one of said screens:
 said first plate is horizontally slidable mounted on said frame, and has a vertical through groove;
 said second plate is vertically slidable mounted on said frame, and has a horizontal through groove;
each one of said screens having:
 a first working position wherein only one of between said first plate and said second plate interferes the line of sight of the eye corresponding to said screen; and
 a second working position wherein said first plate and said second plate interfere the line of sight of the eye corresponding to said plate;
Wherein for said second working position, said vertical groove and said horizontal groove overlap forming a pinhole.

Therefore, the device is advantageous for carrying out the measurements of the design method described above. Since many of the advantages and technical effects described above are equivalent for the device described herein, the repetition thereof will be omitted for the sake of brevity. This way, the device allows positioning with accuracy the location of the screens on each eye, and consequently the pinhole formed by the overlap between the vertical groove and the horizontal groove. Preferably, all the plates are not transparent, which makes it easier for the user to locate the position of the reference object through the through holes. In addition, preferably, the corners of the grooves are beveled, more preferably with a rounded beveling, in order to minimize the effects of diffraction. The person skilled in the art will understand that the device must allow a range of movement of the plates, so that the grooves can be positioned in the whole range of positions necessary so that a user can see a reference object preferably from far vision to near vision. The person skilled in the art will also understand that the size and shape of the device can vary according to the type of user to whom it is intended, so, a device intended only for children will be smaller than one intended only for adults. Preferably, the device is extendable in the horizontal direction so that it can adapt to the morphologies of adult and children users. Preferably, the step between said first working position and said second working position takes place by the vertical movement of said second plate, which minimizes the number of elements and results in a more simplified and, therefore more robust device. Other alternative preferred embodiments comprise hinges for each one of said second plates, so that the change between said first and said second working position comprises making said second plate pivot on said hinges. The person skilled in the art will understand that said plates have a reduced thickness, preferably about 0.5 mm.

Preferably, said first frame supporting means comprise gripping means, configured to attach said device to a spectacles frame on said inner side. This way, the device can adapt to different spectacles frames, which makes it very flexible to use. The gripping means are arranged to support the spectacles frame so that it remains between the user and the device.

In an alternative embodiment, said first frame supporting means comprise arms which in the wearing position extend towards said inner side, and a nasal support, both configured to attach said device to the head of a user. Therefore, the actual device takes the shape of a spectacles frame, so that it can be used directly by the user. This also has the advantage that there is no gap between the device and the frame, and so the holes can be located in the same position where the lenses will go in the wearing position, thus improving accuracy. Said arms are preferably foldable and/or extendable, so that the device can be stored easily, and also so that they can adapt to different user morphologies.

In an alternative embodiment, the device also comprises second frame supporting means, comprising arms and a nasal support, said device having a secondary wearing position wherein said arms extend towards said outer side, said second frame supporting means being configured to attach said device to the head of a user from said outer side. This way, the advantages of previous cases are combined, obtaining a dual device that can both be attached to a spectacles frame and be directly worn by the user. The person skilled in the art will understand that the fact of locating the second supporting means on the inner side and the first supporting means on the outer side is a solution equivalent to the one described herein.

Preferably, said vertical groove has a width comprised between 0.2 mm and 5 mm, preferably between 0.4 mm and 0.6 mm, more preferably 0.5 mm. Preferably, said horizontal groove has a width comprised between 0.2 mm and 5 mm, preferably between 0.4 mm and 0.6 mm, more preferably 0.5 mm, as described above.

Preferably, said first plate is configured to allow, in said first or said second working position, a shift of said vertical groove between 18 mm and 40 mm with respect to the bisecting nasal plane, which results in an advantageous range for adult users. Preferably, the device is extendible in the horizontal direction so that it can adapt to the morphologies of adult and children users.

In an advantageous embodiment, the device also comprises measurement means to determine the position of each one of said grooves. Therefore, it is more comfortable and easier for the professional to obtain the vertical and horizontal position of the resulting pinholes.

Preferably, said measurement means are, each one independently, one of a list consisting of: a scaled ruler, a vernier or a reference for external measurement device. Said reference for an external measurement device is preferably a hole for positioning calipers. Preferably, said means are a vernier, so that the measurement is simple, without the need for external instruments, and at the same time accurate.

Preferably, it also comprises right supporting means configured to support at least one optical element in front of said right screen. Preferably, it also comprises left supporting means configured to support at least one optical element in front of said left screen. Preferably, each one of said at least one optical element is, independently, one of the list consisting of: corrective lenses, colour filters or polarizing filters. This means that the actual instrument can be used to incorporate corrective lenses or to take measurements of associated phoria.

In an advantageous embodiment, said first working position said plate selected from said first plate and said second plate, which interferes the line of sight of the eye, is said first plate. Thus, the device facilitates first determining the horizontal position and then the vertical position.

In another alternative embodiment, said second plate is tiltable between a position parallel to said first plate for said second working position, and a retracted tilted away position for said first working position. This represents the advantage of ensuring minimum interference by the second plate in the first working position.

In a preferred embodiment, said second plate shiftable between a position parallel to said first plate for said second working position, and a retracted shifted away position for said first working position, said retracted shifted away position also being parallel to said first plate. This simplifies the device and makes it less susceptible to mechanical faults.

Preferably, said frame has a general upside-down U shape, with an upper horizontal section, a right vertical section and a left vertical section; so that for said right screen, said first plate is shiftable along a right zone of said horizontal section, and said second plate is shiftable along said right vertical section; and for said left screen, said first plate is shiftable along a left zone of said horizontal section, and said second plate is shiftable along said left vertical section. Therefore, the device has a simple design that allows for a low manufacturing cost and, at the same time it can adapt to the required measurement conditions.

Preferably, each one of said plates is attached to said frame and is shiftable along it by micrometric adjustment means. This confers accuracy to the positioning of the grooves.

Preferably, the position of said right vertical section and the position of said left vertical section can be adjusted horizontally, independently of one another. Thereby allowing the device to adapt to different user morphologies and spectacles frames to which it is attached.

The invention also covers other detailed characteristics illustrated in the detailed description of an embodiment of this invention and in the attached figures.

BRIEF DESCRIPTION OF THE DRAWINGS

The advantages and characteristics of the invention are appreciated from the following description wherein, in a non-limiting way with respect to the scope of the main claim, some preferred embodiments of the invention are explained, referring to the figures.

DETAILED DESCRIPTION OF SOME EMBODIMENTS OF THE INVENTION

Figure 1:
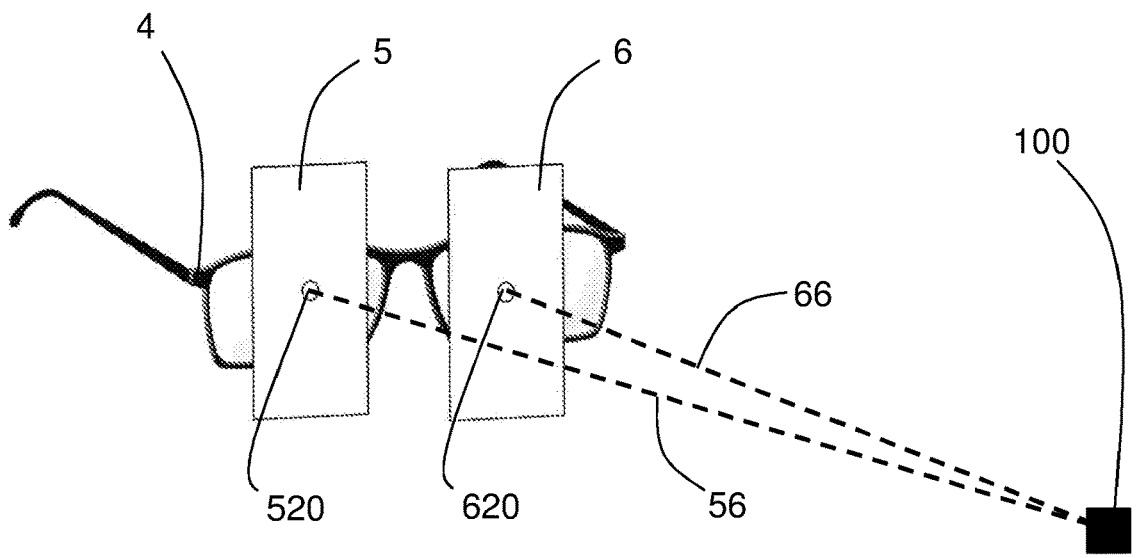
FIG. 1 shows a simplified view of some stages of the method wherein, as a reference, only the spectacles frame and the screens are shown. The dashed lines represent the vision axes.
Figure 2:
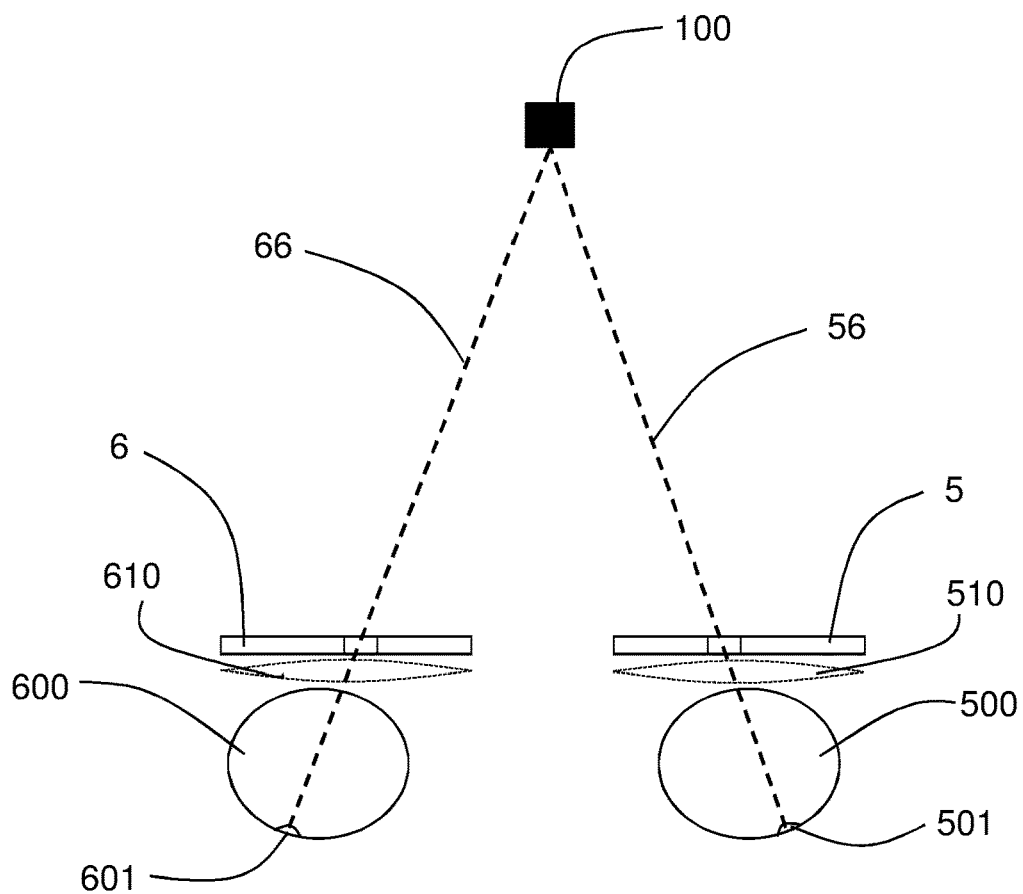
FIG. 2 shows a simplified overhead view of a representation of the elements used in the method of the invention. By way of reference, the wearing position of the lenses is shown with dotted lines, as well as the vision axes marked with dashed lines.

FIGS. 1 and 2 show an embodiment of the method for designing a pair of ophthalmic lenses 510, 610. In a first example, said pair of lenses 510, 610 is intended for lenses for near vision, in particular for reading. Each lens 510, 610 corresponds to an eye 500, 600 of a user. Thus, the right lens 510 corresponds to the right eye 500, and the left lens y 610 corresponds to the left eye 600. FIG. 2 represents diagrammatically the future wearing position of the lenses 510, 610 by means of a dotted line. The method comprises a measurement stage comprising the following steps:

[a] Determining a viewing distance, which in the case of the example is for near vision, and place a reference object 100 at a point located at said viewing distance. The object 100 is placed at the predetermined distance and also at an angle which is preferred for the user according to their preferred posture, in this case, the reading posture. Therefore, as an example, the user is asked to position him or herself in their usual reading posture and the reference object 100 is placed in the place where the eyesight must be focused, for example, in the place where the user would place a book for reading it.

[b] Putting a reference spectacles frame 4 on a user, configured to determine a wearing position of said lenses 510, 610.

[c] For a first eye 500, 600 of the user, as an example, for the right eye 500, although the method is equivalent for the left eye 600:

[1] Keeping said eye 500 uncovered and cover the other eye 600, for the example, the action of covering means closing the eye 600 with the eyelids.

[2] Placing in front of said eye 500 a screen 5 corresponding to said eye 500 having a through hole 520 corresponding to said eye 500. In the example shown in FIGS. 1 and 2 the screen 5 is an opaque card and said hole 520 is a pinhole 55 that has a diameter of 0.5 mm. The hole 520 shown in the figures is not to scale, so that it can be clearly distinguished.

[3] Shifting the position of said hole 520 until the user sees said object 100 looking through said hole 520, so that said object 100 is centred in the field of view that said hole 520 allows, in the case of the example, the hole 520 shifts when the screen 5 having the hole is shifted.

[d] Repeating steps [c.1] to [t c.3] for a second eye. In the case of the example, for the left eye 600. The person skilled in the art will understand that the numeric references in steps [c.1] to [c.3] described above must consequently be modified. For example, for the left eye 600 the other eye corresponds to the right eye 500, the screen 6, and the through hole is 620, which is a pinhole 65 that has a diameter of 0.5 mm.

[e] Uncovering both eyes 500, 600, by opening the eyelids.

[f] In the event that the user sees, in a dissociated way, two areas corresponding to said holes 520, 620 corresponding to said first eye 500 and to said second eye 500 adjusting the position of said holes 520, 620, so that both images fuse, thus obtaining binocular vision. In practice and as an example, the adjustment can be for the two eyes 500, 600 at the same time, or the adjustment can be made for each eye 500, 600 separately, which would be equivalent to repeating some of the steps [c] to [e], or a combination of both solutions. The examples in FIGS. 1 and 2 show the moment when binocular vision is obtained. The person skilled in the art will understand that the steps [c] to [f] have to be made without the user modifying his/her relative position in relation to the reference object 100.

In one embodiment, if the user is not able to fuse both images, the method comprises the following additional steps:

Taking a measurement the associated phoria for said viewing distance.

Determining a prism necessary for said associated phoria.

And repeating the measurement with the presence of said prism, returning to step [c].

In this case, the design of the pair of lenses 510, 610 for the viewing distance is done also according to said prism.

[g] For each hole 520, 620 corresponding to an eye 500, 600 and to a lens 510, 610, taking a measurement of the position of said hole 520, 620 with respect to said wearing position of said lens 510, 610. In the exemplary embodiment, the measurement is directly taken according to the position of each hole 520, 620 with respect to the frame 4. Alternatively, in other embodiments the spectacles frame 4 includes reference lenses, for example lenses with no correction power. In this case, a preferred embodiment is to mark on each reference lens the position of the corresponding hole 520, 620, and then measuring the position of the point marked on each lens.

[h] Design each lens 510, 610 corresponding to an eye 500, 600 for said viewing distance according to said position of said hole 520, 620 corresponding to said eye 500, 600. In the example, the lenses are monofocal lenses 510, 610 for near vision, and their optical centres will be located according to the measured position of said holes 520, 620.

Other embodiments of the method according to the invention are shown below which share a large part of the characteristics described in the preceding paragraphs. Therefore, hereinafter only the differentiating elements will be described, while for the common element reference will be made to the description of the first embodiment.

In another embodiment, said viewing distance corresponds to far vision, so the reference object 100 is placed at a point located in the optical infinity. The person skilled in the art will understand that in the art, in the case of human vision, said optical infinite corresponds to distances starting from 5 m. Therefore, in this example, monofocal lenses 510, 610 are designed for far vision.

In yet another embodiment, the method is carried out first for a first viewing distance, corresponding to far vision, such as the one described above; and secondly for a second viewing distance, corresponding to near vision like the one described in the first example. So, bifocal lenses 510, 610 are designed with two optical centres: one for far vision and one for near vision, each one the result of repeating the method described above. In an example, the lenses 510, 610 are of the type known as progressive bifocal lenses, so that the relative position between both optical centres determines the inset and the length of the corridors of each lens 510, 610.

Figure 3:
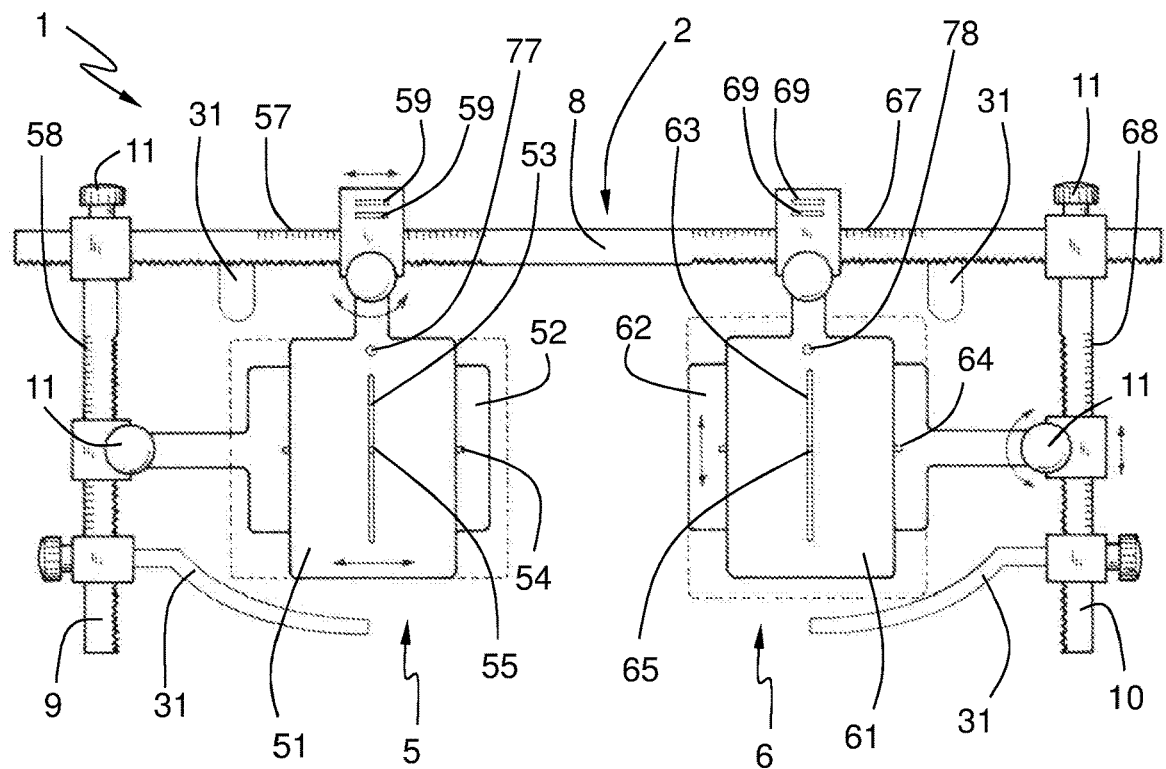
FIG. 3 is a front view of the device according to the invention.
Figure 4:
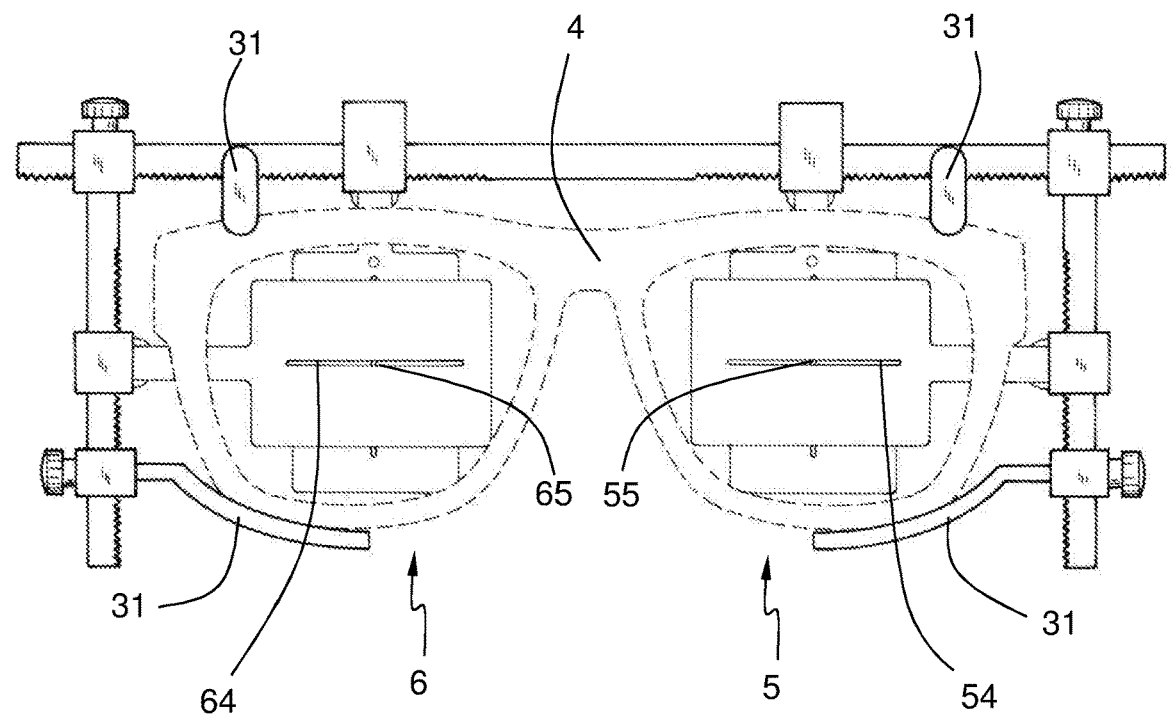
FIG. 4 is a rear view of the device according to the invention wherein, as an example, the reference frame has been shown with dashed lines.
Figure 5:
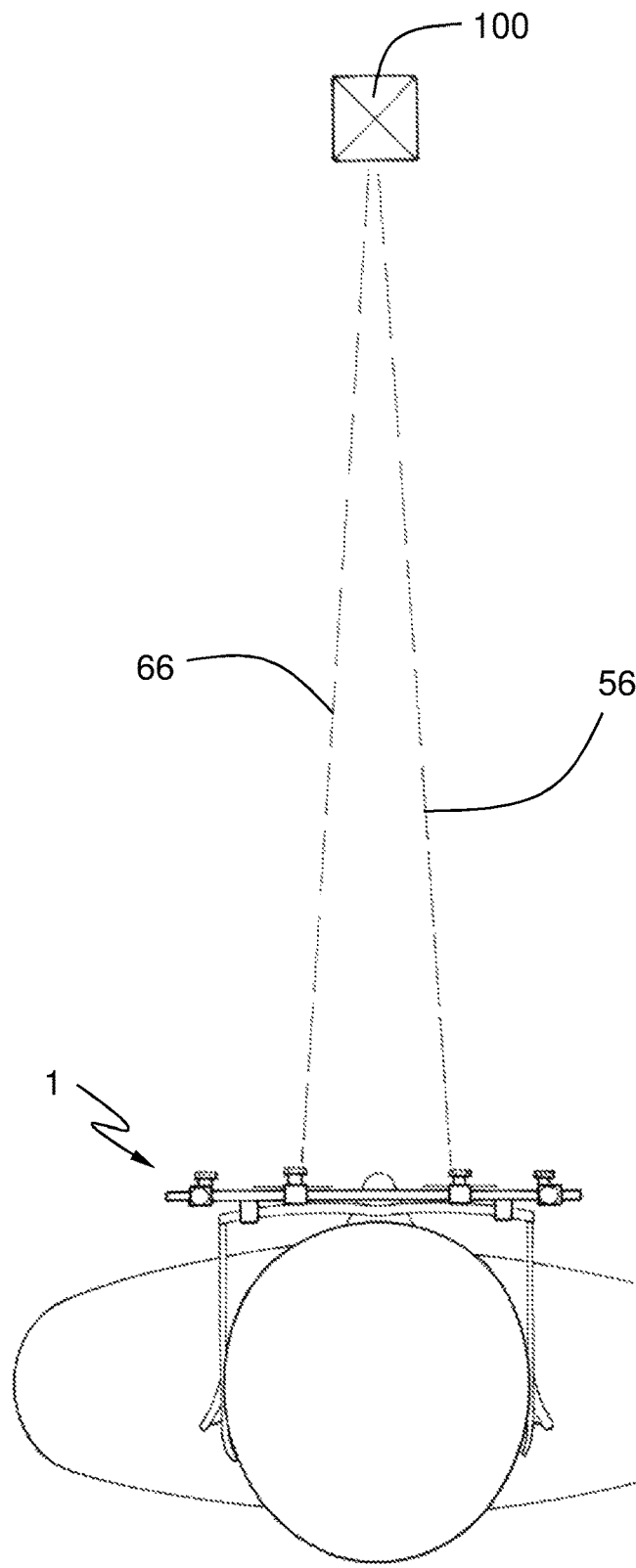
FIG. 5 is an overhead view of the device in use. For the sake of clarity, only some relevant references have been marked.

Another embodiment of the method of the invention uses device 1 shown in FIGS. 3 and 4. In this example, for each eye 500, 600, said screen 5, 6 for said eye 500, 600 comprises a first plate 51, 61, having a vertical through groove 53, 63, and a second plate 52, 62, overlapping said first plate 51, 61 and having a horizontal through groove 54, 64, so that said pinhole 55, 65 is formed by the overlap between said vertical groove 53, 63 and said horizontal groove 54, 64. In the example, all the grooves have a width of 0.5 mm, so that the resulting pinhole 55, 65 in the example has a square profile wherein each side measures 0.5 mm. This way, the right screen 5, comprises a first right plate 51, having a right vertical groove 53. Said first right plate 51 is shiftable in the horizontal direction, so that the shifting of plate 51 serves to position the groove 53. In addition, the right screen 5 also comprises a second right plate 52, which in the working position overlaps the first right plate 51. The second right plate also having a right horizontal groove 54 which when it overlaps the right vertical groove 53 forms a right pinhole 55. The device 1 allows the vertical movement of the second right plate 52, used to position the right horizontal groove 54. The description is equivalent for the left screen 6.

In this embodiment, the steps [c] to [f] break down into a stage for determining the horizontal position and a stage for determining the vertical position. In a preferred embodiment, first the stage for determining the horizontal position is carried out and then the stage for determining the vertical position. In another embodiment, the order is reversed. In some embodiments, the method starts with the user's dominant eye. For the sake of clarity, the example described below considers that the initial eye is the right eye 500, although a person skilled in the art will understand that the method is equivalent if starting with the left eye 600.

Therefore, the stage for determining the horizontal position comprises the following steps:

[c'] For a first eye 500 of the user, as an example, the right eye 500:

[1] Keeping said eye 500 uncovered and cover the other eye 600. In particular, the user closes his/her eyes with his/her eyelids.

[2] Placing said first plate 51 in front of said eye 500.

[3] Shifting said first plate 51 until the user sees said object 100 looking through said vertical groove 53, so that said object 100 is centred in the field of view that said vertical groove 53 allows. In a preferred embodiment, the first plate 51 shifts from a position away from a bisecting nasal plane, in the direction of said plane, which favours locating the object 100 since the vertical groove 53 shifts in the same direction as the eyes when they converge.

[d'] Repeating steps [c'.1] to [c'.3] for a second eye 600, in the case of the example, for the left eye, using the elements corresponding to said left eye 600.

[e'] Uncovering both eyes.

[f'] In the event that the user sees, in a dissociated way, two vertical strips corresponding to said vertical grooves 53, 63, adjusting the position of said first plates 51, 61, so that both images fuse, thus obtaining binocular vision. In some embodiments, if the user is not able to fuse both images, the method comprises the additional steps of measuring the phoria described above. In that case, in some embodiments, the method comprises the additional following steps:

Placing in front of one of the eyes 500, 600, as an example, in front of the right eye 500, a prism having a known prismatic power, said prism overlapped with said hole 520, on the side of said hole 520 furthest from said eye 500.

Repeating the above point with prism having different prismatic powers until making the images from both eyes 500, 600 fuse by adjusting, if it necessary, the position of the vertical grooves 53, 63.

Determining said prism necessary for said associated phoria as the prism that makes the images from both eyes 500, 600 fuse.

On the other hand, the stage for determining the vertical position comprises the following steps:

[c"] For a first eye 500 of a user, as an example, the right eye 500:

[1] Keeping said eye 500 uncovered and covering the other eye 600.

[2] Placing said second plate 52 in front of said eye 500, overlapping said first plate 51.

[3] Shifting said second plate 52 until the user sees the object 100 looking through said pinhole 55, so that said object 100 is centred in the field of view that said pinhole 55 allows.

[d"] Repeating the steps [c".1] to [c".3] for a second eye 600, as an example, the left eye 600.

[e"] Uncovering both eyes.

[f"] In the event that the user sees, in a dissociated way, two visual points corresponding to said pinholes 55, 65, adjusting the position of said second plates 52, 62, so that both images fuse, thus obtaining binocular vision. In some embodiments, if the user is not able to fuse both images, the method comprises the additional steps of measuring the phoria described above.

In some embodiments where the user has phoria, to measure it, previously in the method a colour filter is placed in the line of sight of one of said eyes 500, 600, preferably a red filter.

In an embodiment shown in FIGS. 3 and 4, a device 1 is provided for optical measurements, comprising a frame 2 having a wearing position wherein a user wears said device 1 in front of the eyes 500, 600, defining an inner side facing said eyes 500, 600, and an outer side opposite to said inner side, with said device 1 having first frame supporting means 31, which in the case of the example comprise gripping means 31, configured to attach said device 1 to a spectacles frame 4 on the inner side of the device, i.e., the side closest to the user. FIG. 4 shows the front part of said frame 4 with dashed lines.

The exemplary device 1 also comprises:

A right screen 5, corresponding to the right eye 500, 600 of a user, comprising a first right plate 51 and a second right plate 52.

A left screen 6, corresponding to the left eye 500, 600 of the user, comprising a first left plate 61 and a second left plate 62.

All said plates 51, 52, 61, 62 being made of a non-transparent material.

Also, for each of said screens 5, 6:

Said first plate 51, 61 is horizontally slidable mounted on said frame 2, and has a vertical through groove 53, 63.

Said second plate 52, 62 is vertically slidable mounted on said frame 2, and has a horizontal through groove 54, 64.

In the case of the example, all the plates 51, 52, 61, 62 have a thickness of 0.5 mm, and all the grooves 53, 54, 63, 64, have a width of 0.5 mm.

Each of said screens 5, 6 having:

A first working position wherein only one of between said first plate 51, 61 and said second plate 52, 62 interferes the line of sight 56, 66 of the eye 500, 600 corresponding to said screen 5, 6. In the exemplary embodiment shown in FIGS. 3 to 8, this corresponds to said first plate 51, 61, therefore the horizontal position of the grooves 53, 63 is measured in the first working position.

A second working position wherein said first plate 51, 61 and said second plate 52, 62 interfere the line of sight 56, 66 of the eye 500, 600 corresponding to said screen 5, 6.

Therefore, for said second working position of the exemplary device 1, each of the vertical grooves 53, 63 and its corresponding horizontal groove 54, 64 overlap forming a pinhole 55, 65.

In the same way, in the exemplary embodiment shown in the FIGS. 3 and 4, said second plate 52, 62 is shiftable between a position parallel to said first plate 51, 61 for said second working position, and a retracted shifted away position for said first working position. Said retracted shifted away position also being parallel to said first plate 51, 61. FIG. 3 shows direction arrows that indicate the movement of each plate.

FIGS. 3 and 4 show a device 1 is provided with a frame 2 having a general upside-down U shape, with an upper horizontal section 8, a right vertical section 9 and a left vertical section 10. So, for said right screen 5, said first plate 51 is shiftable along a right zone of the horizontal section 8 by micrometric adjustment means 11 that attach it to said upper horizontal section 8. Besides, said second plate 52 is shiftable along the right vertical section 9 by micrometric adjustment means 11 that attach it to said right vertical section 9. Likewise, for said left screen 6, said first plate 61 is shiftable along a left zone of said horizontal section 8 by micrometric adjustment means 11 that attach it to said upper horizontal section 8. Also, said second plate 62 is shiftable along the left vertical section 10 by micrometric adjustment means 11 which attach it to said left vertical section 10. For the device 1 in the example, each one of the first plates 51, 61 is configured to allow, in the first or the second working position, a shift of its respective vertical through groove 53, 63 between 18 mm and 40 mm with respect to the bisecting nasal plane.

In order to adjust the size of the device 1 for different users, the position of the right vertical section 9 and the position of the left vertical section 10 can be adjusted horizontally, independently of one another.

The device 1 shown in FIG. 3 also comprises measurement means 57, 58, 67, 68 for determining the position of each one of said grooves 53, 54, 63, 64. In the case of the example, a simplified view of a vernier is shown for each one. As an example, FIG. 3 also shows another possible measurement means 77, 78, which in this case comprises a reference for an external measurement device, in particular a small hole 77, 78 into which a caliper can fit.

Other embodiments of the device 1 according to the invention are shown below that share a large part of the characteristics described in the paragraphs above. Therefore, hereinafter only the differentiating elements will be described, while for the common elements reference is made to the description of the first embodiment.

Figure 6:
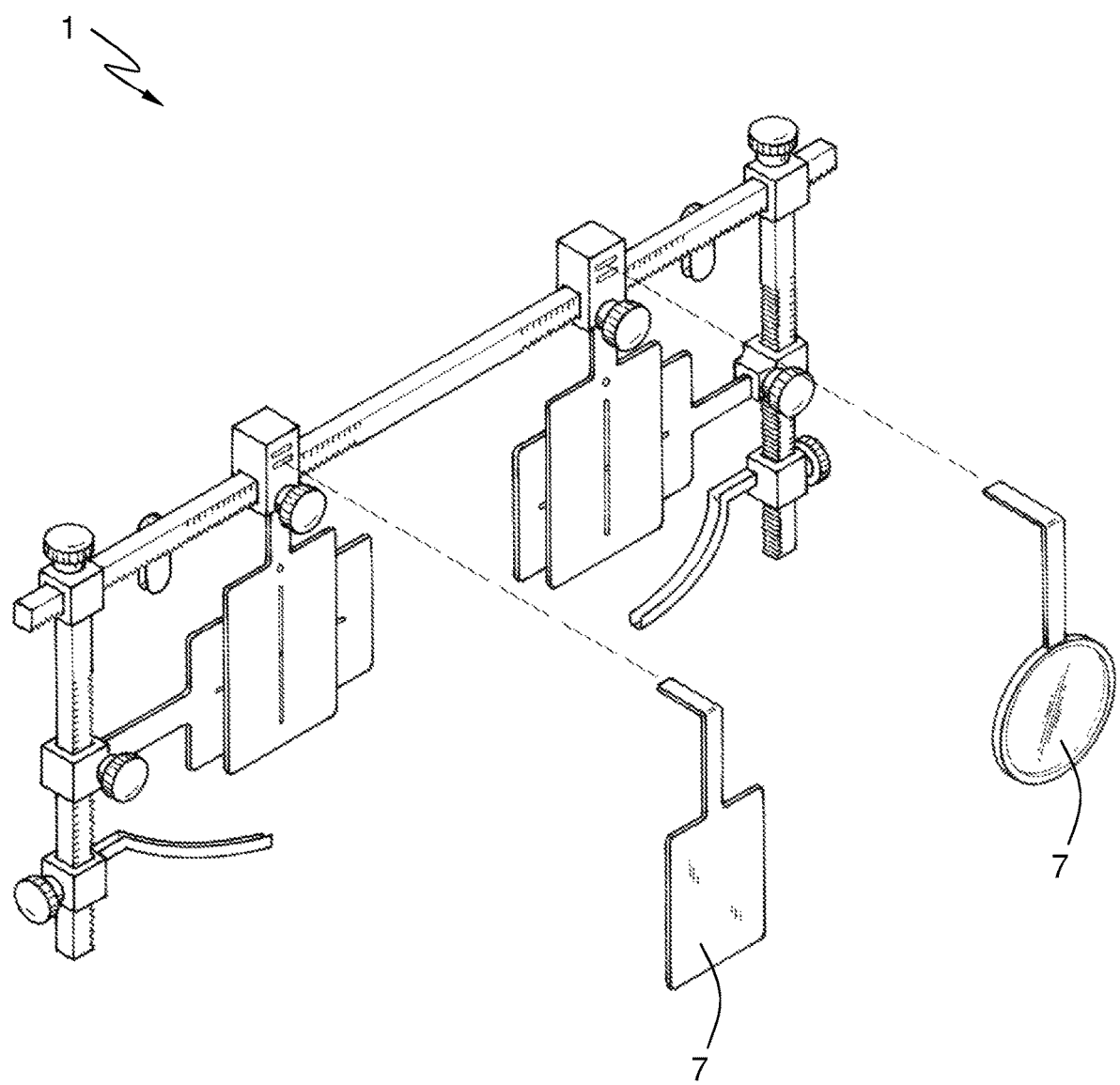
FIG. 6 is a perspective view of the device of the invention.

In the embodiment shown in FIG. 6 the device 1 comprises right supporting means 59 configured to support at least one optical element 7 in front of said right screen 5, and also left supporting means 69 configured to support at least one optical element 7 in front of said left screen 6. Each optical element in the example is, independently of each other, a corrective lens, a colour filter, for example, a red filter, or a polarizing filter. The person skilled in the art will understand that the list described above is not exclusive and can be extended to all kinds of optical elements, which adds versatility to the device 1. For example, the possibility of adding red filters allows using the device for phoria measurements.

Figure 7:
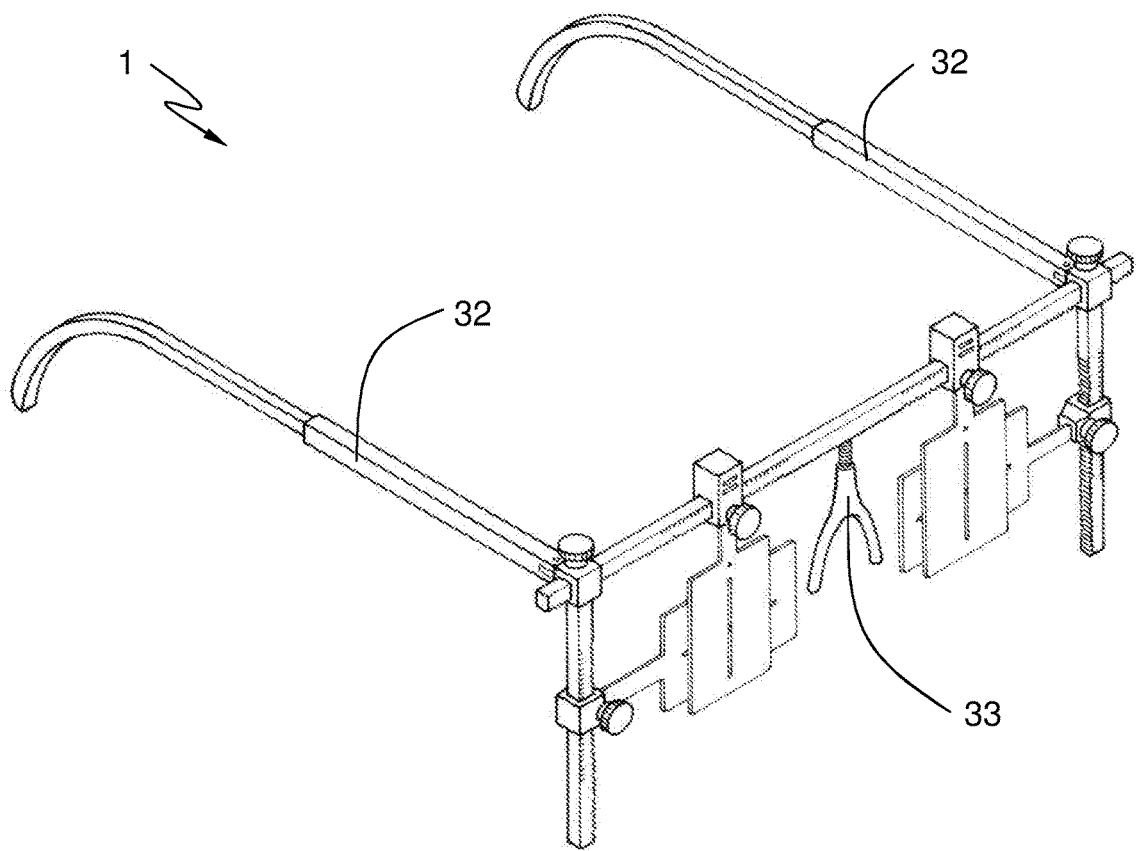
FIG. 7 is a perspective view of an embodiment of the device of the invention able to be worn directly by a user.

FIG. 7 shows another embodiment of the device 1 wherein the first frame supporting means 32, 33 comprise arms 32 which, in the wearing position, extend towards the inner side, and a nasal support 33. Both configured to attach said device 1 to the head of a user. It can be appreciated that it takes the shape of a spectacles frame. The arms in the example are collapsible, so that they can be folded onto themselves, and also extendable so that they can adapt to different user morphologies.

Figure 8:
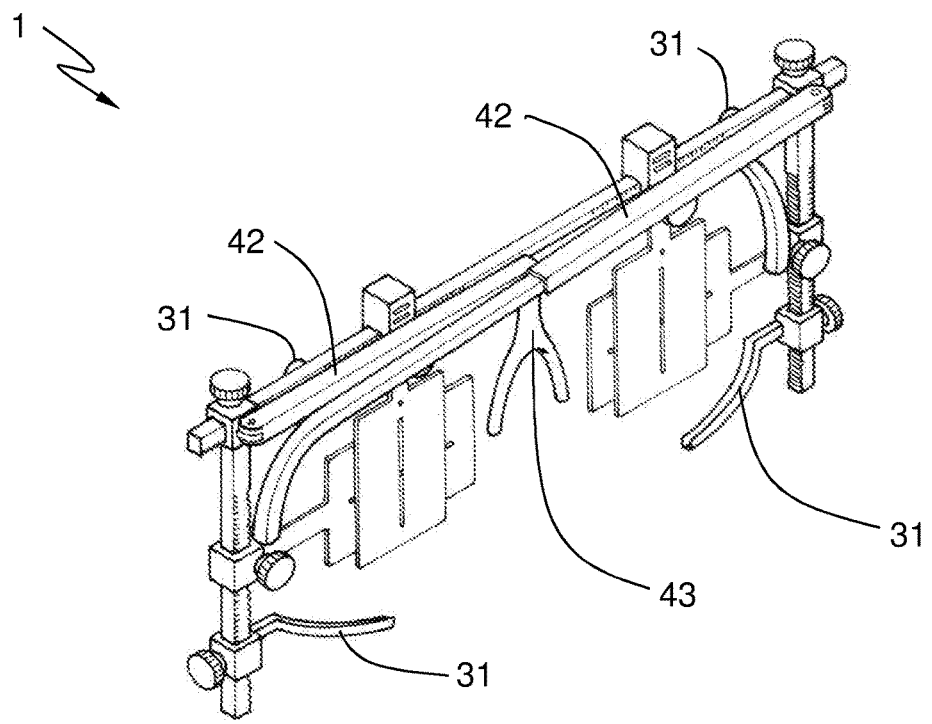
FIG. 8 is a perspective view of another embodiment of the device that comprises both the support for an external spectacles frame and some elements that allow it to be worn directly by a user.

The example in FIG. 8 shows yet another embodiment wherein two types of frame supporting means are combined, one on each side of the device. So the device 1, as well as first frame supporting means in the form of gripping means 31 for attaching the device 1 to a spectacles frame 4, equivalent to FIG. 3 and FIG. 4, also comprises second frame supporting means 42, 43, comprising arms 42 and a nasal support 43, said device 1 having a secondary wearing position wherein said arms 42 extend towards said outer side. Said second frame supporting means 42, 43 being configured to attach said device 1 to the head of a user from said outer side. The person skilled in the art will understand that exchanging the position of both frame supporting means is an equivalent solution to the one described here. As an example, in FIG. 8 the arms 42 of the second frame supporting means are shown in the folded position.

In another embodiment of the device 1 each second plate 52, 62 of the device 1 is tiltable between a position parallel to its corresponding first plate 51, 61, for the second working position, and a retracted tilted away position for the first working position.

The embodiments described herein represent non-limiting examples, so that a person skilled in the art will understand that beyond the examples shown, multiple combinations of the claimed characteristics are possible within the scope of the invention.

The invention claimed is:

1. Method for designing a pair of ophthalmic lenses, each lens corresponding to an eye of a user, comprising a measurement stage comprising the following steps:
    [a] determining a viewing distance and place a reference object at a point located at said viewing distance;
    [b] putting a reference spectacles frame on a user, configured to determine a wearing position of said lenses;
    [c] for a first eye of the user:
        [1] keeping said eye uncovered and covering the other eye;
        [2] placing in front of said eye a screen corresponding to said eye, having a through hole corresponding to said eye;
        [3] shifting the position of said hole until the user sees said object looking through said hole, so that said object is centered in the field of view that said hole allows;
    [d] repeating steps [c.1] to [c.3] for a second eye while maintaining the screen of the first eye in its determined position in which the object is centered in the field of view that said hole allows;
    [e] uncovering both eyes;
    [f] in the event that the user sees, in a dissociated way, two images corresponding to said holes corresponding to said first eye and to said second eye, adjusting the position of said holes so that both images fuse, thus obtaining binocular vision;
    [g] for each hole corresponding to an eye and to a lens, taking a measurement of the position of said hole with respect to said wearing position of said lens; and
    [h] designing each lens corresponding to an eye such that its optical centre for said viewing distance is determined according to said position of said hole corresponding to said eye;
wherein each one of said holes is a pinhole;
wherein for each eye, said screen for said eye comprises a first plate, having a vertical through groove, and a second plate, overlapping said first plate and having a horizontal through groove, so that said pinhole is formed by the overlap between said vertical groove and said horizontal groove, and wherein the steps [c] to [f] break down into a stage for determining the horizontal position of said hole, comprising the following steps:
    [c'] for a first eye of the user:
        [1] keeping said eye uncovered and covering the other eye;
        [2] placing said first plate in front of said eye;
        [3] shifting said first plate until the user sees said object looking through said vertical groove, so that said object is centred in the field of view that said vertical groove allows;
    [d'] repeating steps [c'.1] to [c'.3] for a second eye while maintaining the first plate of the first eye in its determined position in which the object is centered in the field of view that said vertical groove allows;
    [e'] uncovering both eyes; and
    [f'] in the event that the user sees, in a dissociated way, two vertical strip images corresponding to said vertical grooves, adjusting the position of said first plates, so that both vertical strip images fuse, thus obtaining binocular vision;
and a stage for determining the vertical position of said hole, comprising the following steps:
    [c"] for a first eye of a user:
        [1] keeping said eye uncovered and covering the other eye;
        [2] placing said second plate in front of said eye, overlapping said first plate;
        [3] shifting said second plate until the user sees the object looking through said pinhole, so that said object is centred in the field of view that said pinhole allows;
    [d"] repeating steps [c".1] to [c".3] for a second eye while maintaining the first and second plates of the first eye in their determined positions in which the object is centered in the field of view of which said pinhole allows and while maintaining the first plate of the second eye in its determined position in which the object is centered in the field of view that said vertical groove allows;

[e"] uncovering both eyes; and

[f"] in the event that the user sees, in a dissociated way, two visual point images corresponding to said pinholes, adjusting the position of said second plates, so that both visual point images fuse, thus obtaining binocular vision.

2. Method according to claim 1, wherein each one of said pinholes has a diameter between 0.2 mm and 5 mm.

3. Method according to claim 1, wherein in the event that in points [f], [f'] or [f"] the user is not able to get both images to fuse, the method further comprises the following additional steps:

taking a measurement of the associated phoria for said viewing distance;

determining a prism necessary for said associated phoria;

repeating the measurement with the presence of said prism; and designing said pair of lenses for said viewing distance also according to said prism.

4. Method according to claim 3, wherein said measurement of said associated phoria is taken in one of steps [f], [f'] or [f"], comprising the following additional steps:

placing in front of one of the eyes a prism having a known prismatic power, said prism being overlapped with said hole, on the side of said hole furthest from said eye;

repeating the step of placing in front of the eyes a prism by using prisms having different prismatic powers until making the images from both eyes fuse; and determining said prism necessary for said associated phoria as the prism that makes the images from both eyes fuse.

5. Method according to claim 4, wherein prior to step [a] a red colour filter is placed in the line of sight of one of said eyes.

6. Device for optical measurements, comprising a frame having a wearing position wherein a user wears said device in front of the eyes, defining an inner side facing said eyes, and an outer side opposite to said inner side, said device having first frame supporting means, wherein the device also comprises:

a right screen, corresponding to the right eye of a user, comprising a first right plate and a second right plate; and a left screen, corresponding to the left eye of a user, comprising a first left plate and a second left plate, wherein for each one of said screens:

said first plate is horizontally slidable mounted on said frame, and has a vertical through groove;

said second plate is vertically slidable mounted on said frame, and has a horizontal through groove;

each one of said screens having:

a first working position wherein only one of between said first plate and said second plate interferes with the line of sight of the eye corresponding to said screen;

a second working position wherein said first plate and said second plate interfere with the line of sight of the eye corresponding to said screen;

wherein for each of said second working positions, said vertical groove and said horizontal groove overlap forming a pinhole, wherein for each of said screens in said first working position, said plate selected from said first plate and said second plate which interferes with the line of sight of the eye is said first plate, and wherein for each of said screens said second plate is shiftable between a position parallel to said first plate for said second working position, and a retracted shifted away position for said first working position;

wherein for each of said screens said second plate is shiftable between a position parallel to said first plate for said second working position, and a retracted shifted away position for said first working position, said retracted shifted away position also being parallel to said first plate;

wherein said frame has a general upside-down U shape, with an upper horizontal section, a right vertical section and a left vertical section; so that for said right screen, said first plate is shiftable along a right zone of said horizontal section, and said second plate is shiftable along said right vertical section; and for said left screen, said first plate is shiftable along a left zone of said horizontal section, and said second plate is shiftable along said left vertical section; and wherein the position of said right vertical section and the position of said left vertical section can be adjusted horizontally, independently of one another.

7. Device according to claim 6, wherein each one of said vertical grooves has a width between 0.2 mm and 5 mm.

8. Device according to claim 6, wherein each one of said horizontal grooves has a width between 0.2 mm and 5 mm.

9. Device according to claim 6, wherein each of said first right plate and said first left plate is configured to allow, in said first or said second working position, a shift of said vertical groove between 18 mm and 40 mm with respect to the bisecting nasal plane.

10. Device according to claim 6, wherein it also comprises measurement means to determine the position of each one of said grooves.

11. Device according to claim 6, wherein said measurement means are, each one independently, a vernier.

12. Device according to claim 6, wherein it also comprises right supporting means configured to support at least one optical element in front of said right screen.

13. Device according to claim 6, wherein it also comprises left supporting means configured to support at least one optical element in front of said left screen.

14. Device according to claim 13, wherein each one of said at least one optical element is, independently, one of a list consisting of: corrective lenses, colour filters or polarizing filters.

15. Device according to claim 12, wherein each one of said at least one optical element is, independently, one of a list consisting of: corrective lenses, colour filters or polarizing filters.

16. Device according to claim 6, wherein each one of said plates is attached to said frame and is shiftable along it by micrometric adjustment means.

17. Device for optical measurements, comprising a frame having a wearing position wherein a user wears said device in front of the eyes, defining an inner side facing said eyes, and an outer side opposite to said inner side, said device having first frame supporting means, wherein the device also comprises:

a right screen, corresponding to the right eye of a user, comprising a first right plate and a second right plate; and a left screen, corresponding to the left eye of a user, comprising a first left plate and a second left plate, wherein for each one of said screens:

said first plate is horizontally slidable mounted on said frame, and has a vertical through groove;

said second plate is vertically slidable mounted on said frame, and has a horizontal through groove;

each one of said screens having:

a first working position wherein only one of between said first plate and said second plate interferes with the line of sight of the eye corresponding to said screen;

a second working position wherein said first plate and said second plate interfere with the line of sight of the eye corresponding to said screen;

wherein for each of said second working positions, said vertical groove and said horizontal groove overlap forming a pinhole, wherein for each of said screens in said first working position, said plate selected from said first plate and said second plate which interferes with the line of sight of the eye is said first plate, and wherein for each of said screens said second plate is shiftable between a position parallel to said first plate for said second working position, and a retracted shifted away position for said first working position; and wherein for each of said screens said second plate is tiltable between a position parallel to said first plate for said second working position, and a retracted tilted away position for said first working position.

18. Method for designing a pair of ophthalmic lenses, each lens corresponding to an eye of a user, comprising a measurement stage comprising the following steps:

[a] determining a viewing distance and place a reference object at a point located at said viewing distance;

[b] putting a reference spectacles frame on a user, configured to determine a wearing position of said lenses;

[c] for a first eye of the user:

[1] keeping said eye uncovered and covering the other eye;

[2] placing in front of said eye a screen corresponding to said eye, having a through hole corresponding to said eye;

[3] shifting the position of said hole until the user sees said object looking through said hole, so that said object is centred in the field of view that said hole allows;

[d] repeating steps [c.1] to [c.3] for a second eye while maintaining the screen of the first eye in its determined position in which the object is centered in the field of view that said hole allows;

[e] uncovering both eyes;

[f] in the event that the user sees, in a dissociated way, two images corresponding to said holes corresponding to said first eye and to said second eye, adjusting the position of said holes so that both images fuse, thus obtaining binocular vision;

[g] for each hole corresponding to an eye and to a lens, taking a measurement of the position of said hole with respect to said wearing position of said lens; and

[h] designing each lens corresponding to an eye such that its optical centre for said viewing distance is determined according to said position of said hole corresponding to said eye;

wherein each one of said holes is a pinhole;

wherein for each eye, said screen for said eye comprises a first plate, having a vertical through groove, and a second plate, overlapping said first plate and having a horizontal through groove, so that said pinhole is formed by the overlap between said vertical groove and said horizontal groove.

* * * * *